United States Patent [19]
Peers-Trevarton

[11] 4,259,962
[45] Apr. 7, 1981

[54] SEALING SYSTEM FOR CARDIAC PACER LEAD CONNECTOR

[75] Inventor: Charles A. Peers-Trevarton, Coral Springs, Fla.

[73] Assignee: Cordis Corporation, Miami, Fla.

[21] Appl. No.: 69,535

[22] Filed: Aug. 24, 1979

[51] Int. Cl.³ .............................................. A61N 1/00
[52] U.S. Cl. ................................................. 128/419 P
[58] Field of Search ..................... 128/419 P, 784–786

[56] References Cited
FOREIGN PATENT DOCUMENTS
2810004 9/1978 Fed. Rep. of Germany ........... 128/786

Primary Examiner—William E. Kamm
Attorney, Agent, or Firm—Kenway & Jenney

[57] ABSTRACT

A tubular connector for a cardiac pacer lead assembly has axially spaced inner and outer rings for sealing engagement with the wall of a pacer neck, and grooves outwardly adjacent the rings. As the rings are deflected backwardly when the lead is inserted into the pacer neck, they overlay the grooves. Any fluid trapped under pressure between the rings will act to press the inner ring into greater sealing engagement with the wall of the pacer neck.

8 Claims, 5 Drawing Figures

SEALING SYSTEM FOR CARDIAC PACER LEAD CONNECTOR

BACKGROUND OF THE INVENTION

The present invention relates generally to lead assemblies for use with cardiac pacer apparatus, and more particularly to improved sealing systems for lead connectors in cardiac pacer necks.

In the ordinary use of cardiac pacers, it is desirable to place the cardiac pacer circuitry and batteries in an apparatus located in the body but remote from the heart to have more room and to facilitate replacement of the pacer upon depletion of its batteries. A flexible lead is usually provided to connect this pacer apparatus to the desired stimulation site in the heart. Adequately attaching one end of this flexible lead to heart muscle tissue is one concern of the art. Another, with which this invention is concerned, is the safe and secure attachment of the other end of the lead to the pacer apparatus.

This connection is ordinarily accomplished by the insertion of an exposed terminal pin of the lead into an electrical terminal in the neck of the pacer apparatus, the electrical terminal being set inside a cylindrical bore through the pacer neck. The lead is disposed normally in a tubular connector which must sealingly engage the inside wall of the cylindrical bore to maintain free of body fluids the connection between the lead terminal pin and the pacer terminal. Leakage of body fluids beyond the bore into the terminal connection would adversely affect the connection; an adequate and durable seal against such leakage must be maintained.

One approach of the prior art is to provide a pair of compressible rings, axially spaced apart, on the tubular connector coaxially supporting the terminal pin. Such a system is shown, for example, in U.S. Pat. No. 4,072,154. Since the sealing rings must have some extra compressibility to allow ease in the insertion of the lead into the pacer apparatus, however, body movement may cause pivotal movement of the tubular connector in the pacer neck.

If the outermost ring in such a system loses sealing contact with the pacer neck bore because of such movement, body fluids may seep past it. In such cases, the innermost seal generally does not break contact with the inner wall of the bore since the turning moment acting upon it is small and the normal compressibility of the elastomer of which the connector is made maintains a sealed interface. However, if body fluids do leak past the outermost seal, when that seal returns to its predeflected state it may act as a pump and compress the trapped fluid, forcing it forward past the inner seal.

Accordingly, it is an object of the invention to provide a pacer lead sealing system that reduces the possibility of body fluid leaking past, and allows greater pivotal movement of the connector without breakdown of the seal.

Other objects of the invention are to allow for wider manufacturing tolerances for the seals without reducing or jeopardizing their effectiveness, to allow greater seal pressures to be achieved without increasing the force necessary to insert the connector, to reduce the deleterious effect of minor imperfections on the inside pacer neck aperture wall, and to utilize the compression of body fluids that may have leaked past the outer seal to increase the strength of the inner seal rather than weaken it.

Other objects and features of the invention will in part be apparent and in part be pointed out hereinafter.

SUMMARY OF THE INVENTION

The invention provides for a resiliently deflectable ring about the tubular connector for sealing engagement with the wall of the pacer bore into which the connector is inserted. The connector includes a groove located outwardly adjacent the ring, which the ring partially overlays when it is deflected. More than one such combination of ring and groove, the combinations axially spaced apart along the connector, may be used. Such a ring forms a truncated hollow cone, and fluid under pressure trapped outwardly of the ring and occupying the groove will tend to press the ring into further sealing engagement with the pacer wall.

BRIEF DESCRIPTION OF THE DRAWING

For a fuller understanding of the nature and objects of the invention reference should be made to the following detailed description and the accompanying drawings in which.

Corresponding reference characters indicate corresponding parts throughout the several views of the drawings.

DESCRIPTION OF THE PREFERRED EMBODIMENT

Figure 1:
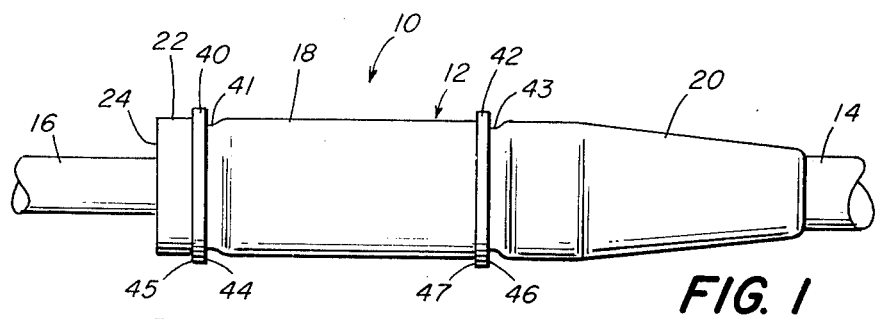
FIG. 1 is an elevation view of a portion of a pacer lead, showing the sealing connection embodying the invention.

Referring now to FIG. 1, there is shown a cardiac pacer lead assembly generally designated 10, constructed in accordance with the present invention. Except for the sealing system, the general construction of the lead assembly 10 is conventional. The assembly 10 is generally an elongated tubular structure formed of a connector 12 within and through which is disposed the end of the cardiac pacer lead 14, including the lead terminal pin 16.

The connector 12 is molded from a resilient elastomer or some other suitable rubber-like material. It has an inside distal portion 18 that is generally cylindrical and an outside proximal portion 20 that tapers from the outer end of portion 18 to near lead 14. The inner end portion 22 of the connector 12 is a flat disc-like portion with a flat surface 24.

Figure 2:
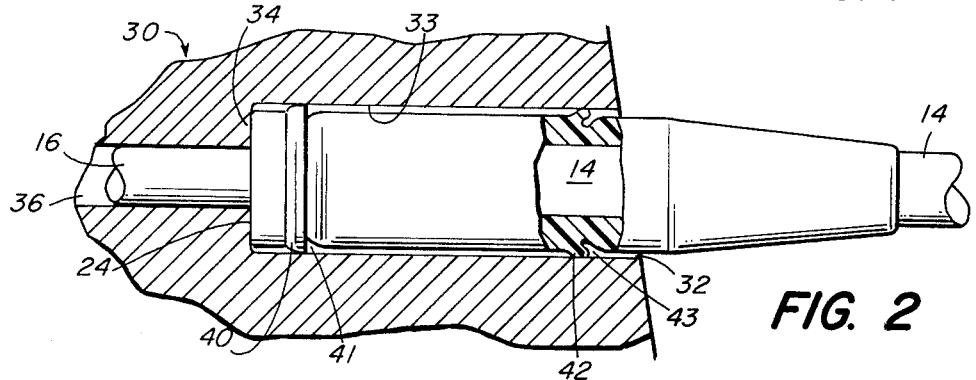
FIG. 2 shows the same portion of the lead inserted into the aperture of the neck of a pacer apparatus.

The cardiac pacer neck 30 to which the lead assembly 10 will be connected is shown in FIG. 2 in section. The neck 30 has a cylindrical bore defining an aperture 32 with an inside wall 33 for receiving the lead connector 12, terminating inside with a shoulder portion 34, and a stepped down bore 36 for receiving the terminal pin 16 of the lead 14 for connection to a terminal inside the pacer neck 30 but shown in the drawing.

Returning to FIG. 1, the molded elastomeric connector 12 is shown to have two rings 40 and 42 formed at either end of the cylindrical portion 18. The inner ring 40 is located back a small distance from the front surface 24 of the inner end of the connector. The outer ring 42 is located near the other, outer, end of the connector cylindrical portion 18. The location of the rings 40 and 42 are selected to conform to the aperture 32 of the pacer neck 30 in that one will be located close to inside end of the aperture and the other close to the outside end, when the lead is inserted.

Each of the rings 40, 42 has an outside diameter larger than the inside diameter of the aperture 32. The elastomeric nature of the connector 12 of which the rings are a part results in the rings being flexible and resiliently deflectable in the axial direction.

The connector 12 furthermore has annular undercut spaces defining a groove 41 and groove 43 just beyond each of the rings 40 and 42 respectively. The grooves 41 and 43 are about as deep into the cylindrical body portion 18 of the connector as the rings 40 and 42 are high above it. The grooves 41 and 43 are just outwardly adjacent the back of rings 40 and 42 so that, in effect, the rings 40 and 42 have back surfaces 44 and 46, respectively, that have radial depths about twice as great as those of the inwardly facing front surfaces 45 and 47, respectively.

In use, the lead assembly 10 is inserted into the aperture 32 of the cardiac pacer neck 30 until the front surface of the connector 12 meets the shoulder 34 at the inside end of the aperture. The pin 16 projecting from the front of the connector 12 extends into the aperture 36 and to the connection with the terminal (not shown) inside the pacer apparatus.

As a result of the insertion, the large diameter rings 40 and 42 projecting from the connector 12 are deflected back as the connector enters the aperture 32, their resilience urging the inner facing surfaces 45 and 47 into sealing contact with the inside wall 33 of the aperture, as seen in FIG. 2.

The rings 40 and 42, it should be noted, are not merely compressed radially after insertion. Rather they are compressed and also deflected backwardly by the insertion, occupying partially the space provided by the grooves 41 and 43 just behind them. The partial sectional view of FIG. 2 illustrates the effect, showing the outermost ring 42 deflected back by the aperture wall 33 and overlaying the groove 43. Because of the deflection, the outside diameters of the rings 40 and 42 may be larger than that of, for example, an ordinary O-ring, which is simply slightly compressed in forming a circular seal. O-rings therefore do not have too great an outside diameter for cylindrical apertures and manufacturing tolerances are small. The manufacturing tolerances for the outside diameter of rings 40 and 42 may be greater, and greater variations in the pacer neck aperture wall 33 may also be tolerated.

After insertion, each ring 40 and 42 of the connector 12 will deflect backwards and form a truncated hollow cone whose hollow large-diameter end is directed toward the outside of the pacer neck 30. The deflection from ring to truncated cone is aided by the presence of the annular under-cut spaces represented by the grooves 41 and 43 into which the deflected mass of the rings can move.

Figure 3:
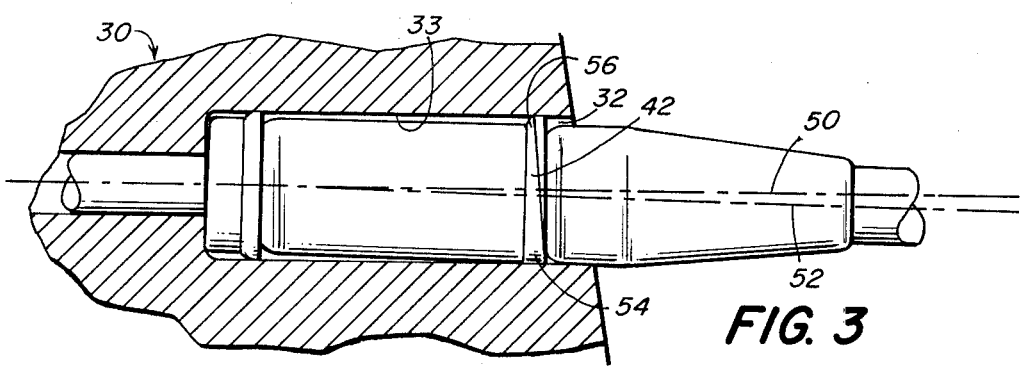
FIG. 3 shows the lead in the pacer neck, pivotally displaced.

FIG. 3 illustrates the effect on the sealing system of pivotal movement of the connector 12 in the pacer neck aperture 32. Dotted line 50 represents the axis of the aperture 32. Dotted line 52 represents the axis of the connector 12. The relative displacement of the two axes which results from movement of the patient's body, or movement of the pacer apparatus, causes one side of a ring to compress and deflect even more (for example, side 54 of outermost ring 42 in the example shown). The other side of the ring (side 56 in the example) will, however, remain in sealing contact with the wall 33 of the pacer aperture 32, because as the ring 42 becomes less deflected, it tends to change its configuration from a cone back to a ring. This "memory" characteristic of the resiliently deflectable ring 42 results in the side 56 facing the wall 33 remaining in contact with the wall, at least until the ring configuration of the ring 42 is restored.

Figure 5:
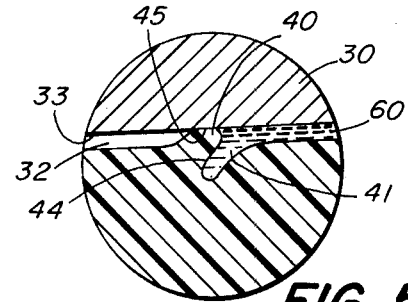
FIG. 5 is a detailed view of a portion of the region shown in FIG. 4.
Figure 4:
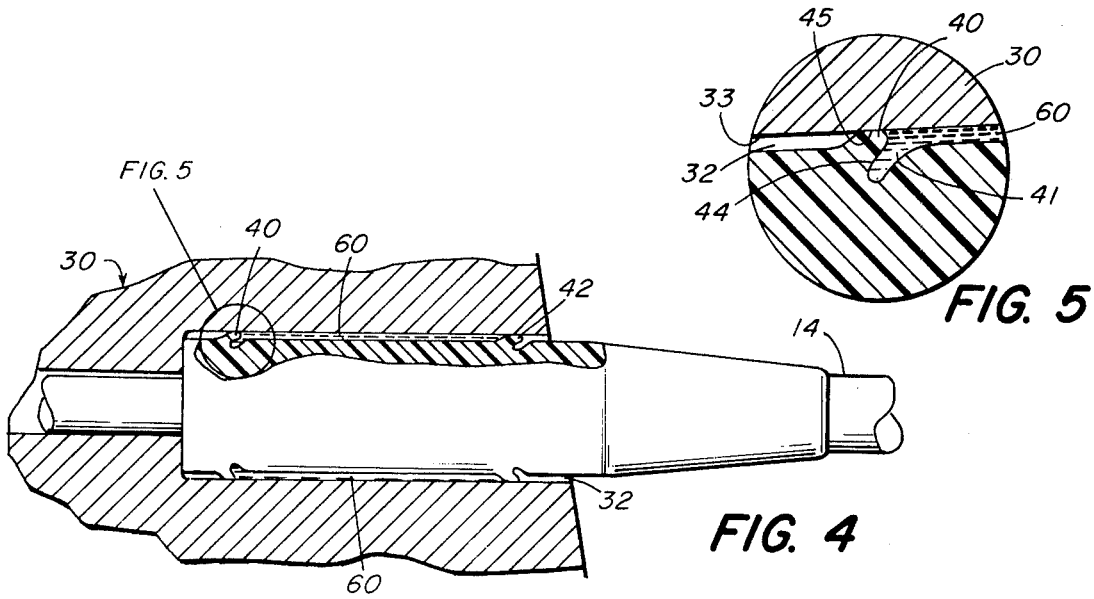
FIG. 4 shows the lead in the pacer neck, after body fluid has entered the region between the outer and inner seals.

Since the efficiency and tightness of a connector seal is by necessity a compromise between the radial pressure which it exerts against the aperture wall and the ease with which it can be inserted into the aperture, there is the possibility that, due to extreme body or pacer motion the limits of the sealing system will be reached and that the outer seal ring 42 will part contact with the aperture wall 33 and allow body fluid 60 to seep past it (See FIGS. 4 and 5).

As with conventional seals, when the outer seal 42 is restored to its central, sealing position, any body fluids 60 which may have leaked past it will be compressed. With the sealing system of the invention, however, when the fluid pressure is detected by the front coned seal ring 40, it is exerted in the inside hollow area of the cone, formed by the deflected ring overlaying, in the radial direction, the annular undercut space, or groove, 41. As can be seen from the detailed view in FIG. 5, body fluid 60 entering this space 41 forms a ring of fluid under pressure which expands and exerts a radial pressure in the direction of the arrows on the surface 44 of the ring 40 overlaying the space, forcing the inner surface 45 of the ring 40 into tighter contact with the wall 33 of the aperture 32.

It is apparent from the foregoing description of the preferred embodiment that the several objects of the invention are achieved and that other advantageous results have been attained.

As various changes could be made in the above constructions without departing from the scope of the invention, it should be understood that all matter contained in the above description or shown in the accompanying drawing shall be interpreted as illustrative and not in a limiting sense.

What is claimed is:

1. A cardiac pacer lead assembly for use with a cardiac pacer apparatus having an electrical terminal at the inner end of a cylindrical bore for reception of an electrical lead, comprising:

a generally tubular connector means for insertion into said cylindrical bore, through which may be disposed an electrical lead for connection to said terminal, said connector means having a resiliently deflectable ring on the exterior of said connector means, said ring having an outside diameter in an undeflected position greater than the inside diameter of said bore, said connector means further defining an annular groove means outwardly immediately adjacent said ring having an inside diameter less than that of said tubular connector means said ring being deflectable over said groove means upon insertion of said connector means into said cylindrical bore.

2. The cardiac pacer lead assembly as claimed in claim 1 in which said connector means has an additional ring axially spaced from said ring and similar to said ring, and said connector means furthermore defines an additional groove similar to said annular groove means, adjacent said additional ring.

3. The lead assembly of claim 1 in which said connector means is an integral molded elastomeric unit.

4. A cardiac pacer lead assembly for use with a cardiac pacer apparatus having an electrical terminal inwardly of a cylindrical bore, for reception of an electrical lead, comprising:
   tubular elastomeric connector means for coaxial insertion inwardly into said bore and for sealing engagement with the inside wall of said cylindrical bore,
   and electrical lead means coaxially disposed within said connector means for connection with said terminals,
   wherein the improvement comprises said connector means having:
      a ring means for sealing engagement with said wall, said ring having an outside diameter greater than the diameter of said bore and being resiliently deflectable axially outwardly when said assembly is inserted into said bore, and
      a surface portion defining an annular undercut space outwardly immediately adjacent said ring having an inside diameter less than that of said tubular connector means for providing space into which said ring may be deflected partially upon insertion of said assembly into said bore so that said ring overlays said annular space.

5. The lead assembly as claimed in claim 4, having more than one combination of said ring means and outwardly adjacent undercut space, each ring and space combination being axially spaced from the others.

6. A cardiac pacer lead assembly for use with a cardiac pacer apparatus having an electrical terminal inwardly of a cylindrical bore, for reception of an electrical lead, comprising:
   tubular elastomeric connector means, having inward and outward end portions, for coaxial insertion inwardly into said bore for sealing engagement with the inside wall of said bore, and
   electrical lead means coaxially disposed within said connector means for connection with said terminal, said connector means comprising:
      a first ring means for sealing engagement with said wall, said first ring means having an outside diameter greater than the diameter of said bore, and being resiliently deflectable axially outwardly when said assembly is inserted into said bore, said first ring means being located near said connector inward end portion,
      a first surface portion defining a first annular undercut space outwardly immediately adjacent said first ring means, said annular space having an inside diameter less than the diameter of said connector means,
      said first ring means being deflectable over said annular space when said assembly is inserted into said bore
      a second ring means for sealing engagement with said wall, said second ring means being resiliently deflectable axially outwardly when said assembly is inserted into said bore, said second ring means being located near said connector outward end portion, and
      a second surface portion defining a second annular undercut space outwardly adjacent said second ring means.

7. A cardiac pacer lead assembly for use with a cardiac pacer apparatus having an electrical terminal inwardly of a cylindrical bore, for reception of an electrical lead, comprising:
   tubular elastomeric connector means, having an inner end portion and an outer end portion, insertable into said bore, and
   electrical lead means disposed axially within said connector means for connection with said terminal, said connector means including:
   an inner ring means located near said connector inner end portion, having an outside diameter greater than the inside diameter of said cylindrical bore, for sealing engagement with the wall of said bore, said inner ring means being resiliently deflectable axially outwardly when said assembly is inserted into said bore, and having an annular axially inwardly facing surface,
   and an inner surface portion defining an inner annular undercut space having an inside diameter less than that of said tubular connector means, outwardly immediately adjacent said inner ring means said inner ring being axially outwardly deflectable to overlay said undercut annular space upon insertion of said assembly into said bore to form a truncated hollow cone with said annular axially inwardly facing surface sealingly engaging said bore wall.

8. The cardiac pacer lead assembly of claim 7 further including said connector means having outer sealing ring means located near said connector outer end portion.

* * * * *